US008323691B2

(12) United States Patent
Geerke et al.

(10) Patent No.: US 8,323,691 B2
(45) Date of Patent: Dec. 4, 2012

(54) METHODS AND APPARATUS FOR DETERMINING FORMULATION ORIENTATION OF MULTI-LAYERED PHARMACEUTICAL DOSAGE FORMS

(75) Inventors: Johan H. Geerke, Los Altos, CA (US); Steven F. Stone, Saratoga, CA (US)

(73) Assignee: Alza Corporation, Palo Alto, CA (US)

( * ) Notice: Subject to any disclaimer, the term of this patent is extended or adjusted under 35 U.S.C. 154(b) by 782 days.

(21) Appl. No.: 12/402,075

(22) Filed: Mar. 11, 2009

(65) Prior Publication Data

US 2009/0186085 A1    Jul. 23, 2009

Related U.S. Application Data

(62) Division of application No. 09/324,343, filed on Jun. 2, 1999, now Pat. No. 7,521,067.

(60) Provisional application No. 60/087,787, filed on Jun. 3, 1998.

(51) Int. Cl.
*A61K 9/24* (2006.01)
*A61K 9/62* (2006.01)
*G01J 3/46* (2006.01)

(52) U.S. Cl. .................. 424/473; 424/461; 356/402
(58) Field of Classification Search .................. None
See application file for complete search history.

(56) References Cited

U.S. PATENT DOCUMENTS

| 5,089,270 | A | 2/1992 | Hampton et al. |
| 5,094,786 | A | 3/1992 | Nagashima et al. |
| 5,248,310 | A | 9/1993 | Barclay et al. |
| 5,294,770 | A | 3/1994 | Riddle et al. |
| 5,399,828 | A | 3/1995 | Riddle et al. |
| 5,422,831 | A | 6/1995 | Misra et al. |
| 5,464,631 | A | 11/1995 | Hoover et al. |
| 5,558,231 | A | 9/1996 | Weier |
| 5,582,838 | A | 12/1996 | Rork et al. |
| 5,785,994 | A * | 7/1998 | Wong et al. .................. 424/473 |
| 5,824,338 | A | 10/1998 | Jacobs et al. |
| 7,521,067 | B1 | 4/2009 | Geerke et al. |

* cited by examiner

*Primary Examiner* — Sreeni Padmanabhan
*Assistant Examiner* — Jody Karol
(74) *Attorney, Agent, or Firm* — Woodcock Washburn LLP

(57) ABSTRACT

Rapid and accurate determination of the formulation orientation of multi-layer capsule-shaped tablets with respect to different internal formulation layers proximate to the opposite narrow and rounded ends of the tablets is required. By including an appropriate color scheme in multi-layer osmotic tablets, detection of the formulation orientation is achieved by detecting the color at a spot location on a side of the tablet corresponding to one or another formulation layer or to one or another interface of two formulation layers depending on the formulation orientation of the tablet.

24 Claims, 2 Drawing Sheets

METHODS AND APPARATUS FOR DETERMINING FORMULATION ORIENTATION OF MULTI-LAYERED PHARMACEUTICAL DOSAGE FORMS

CROSS-REFERENCE TO RELATED APPLICATIONS

This application is a divisional of U.S. Ser. No. 09/324,343, filed Jun. 2, 1999 (now allowed), which claims priority of Provisional application Ser. No. 60/087,787, filed Jun. 3, 1998, the contents of each of which are herein incorporated by reference in their entirety.

BACKGROUND OF THE INVENTION

1. Field of the Invention

This invention pertains to pharmaceutical manufacturing and particularly to determining the formulation orientation of multi-layer capsule-shaped tablets with respect to different internal formulation layers proximate to the opposite narrow and rounded ends of the tablets. In particular, the present invention pertains to rapidly and accurately determining the formulation orientation of such tablets by including a specific color scheme in the multi-layer design of the tablets that permits color detection at a spot location on the side of the tablet to be used for determining the formulation orientation.

2. Description of the Related Art Including Information Disclosed Under 37 CFR 1.97 and 1.98

Colorants may be used as an indicator of different formulation layers in multi-layer dosage forms. Formulating different formulation layers with different colorants is a useful quality control method that helps ensure that the different formulation layers are distinguishable from each other during the manufacturing process. Different colors included in the different layers can be used to determine the formulation orientation of the dosage form with respect to the internal formulation layers when such a determination is required for a particular processing step. An example of such a processing step is drilling of a delivery port in a multi-layer osmotic dosage form. These dosage forms have an internal compartment containing at least one drug-containing layer, at least one expandable polymer-containing layer and, optionally, one or more drug-free layers to produce a desired release pattern such as delayed or pulse release. The internal compartment is surrounded by a membrane that is at least partially semipermeable and at least one delivery port is formed through the membrane at an appropriate location to permit release of drug-containing formulation from within the compartment. The expandable polymer-containing layer is known as a "push" layer because, following oral administration, fluid is imbibed through the semipermeable membrane causing the drug-containing layer(s) and any optional drug-free layer(s) to form a dispensable formulation and causing the polymer layer to expand and "push" the dispensable formulation through the delivery port.

Such osmotic dosage forms are typically manufactured by compressing the component dispensable formulation-forming layer(s) and the push layer(s) together to form a multi-layer internal core, applying the semipermeable membrane around the core and then drilling, typically with a laser, an appropriate delivery port. It will be appreciated that these dosage forms are internally non-symmetrical in that one or more portions contain the dispensable formulation-forming layer(s) and one or more portions contain the push layer(s). Generally, the push layer is adjacent to one end, the "push end," of the tablet and the opposite end is the "dispensing end" that is proximal to the dispensable formulation-forming layer(s) within the dosage form. Proper operation of the dosage form requires that the delivery port be formed in the dispensing end of the dosage form and not in the push end of the dosage form. Thus, at some point prior to the laser drilling step, the internal formulation orientation of the dosage forms with respect to these opposite ends must be determined to ensure that the delivery port is drilled in the dispensing end, and not the push end, of each tablet.

Typically, multi-layer osmotic tablets have been produced in conventional tablet shapes such that a broad front surface encompasses the dispensing end of the tablet and the opposite broad back surface encompasses the push end of the tablet. By including a colorant in at least one formulation layer proximate to either the dispensing end or the push end of the tablet, a contrast or color detector can be used to determine the formulation orientation of the tablets with respect to the front and back surfaces. Useful methods and apparatus for determining the formulation orientation of such tablets and for drilling the delivery ports in the dispensing ends of the tablets are disclosed and claimed in U.S. Pat. Nos. 5,294,770 and 5,399,828 owned by Alza Corporation, each of which is incorporated in its entirety by reference herein. In accord with these inventions, multi-layer osmotic tablets are supplied in a manner that permits laser access to both the front and the back surface of the dosage form. A suitable color detector is used to determine which surface encompasses the dispensing end of the tablet and, then, a laser controller directs the laser to drill at least one delivery port in that end.

The above-described methods have been shown to be especially satisfactory for conventional tablet shapes where the dispensing end and the push end of the tablet coincide with the front and back surfaces of the tablet. Because these surfaces are relatively broad and flat, a color detector is able to accurately and rapidly determine the color and generate an appropriate signal to direct the laser. More recently, it has been discovered that capsule-shaped osmotic tablets having the dispensing end at one narrow and rounded end of the capsule-shaped tablet and the push end is at the opposite narrow and rounded end of the capsule-shaped tablet are preferable to conventional tablet shapes for certain applications. Unfortunately, because the narrow and rounded ends of the capsule-shaped tablets scatter a significant portion of light directed thereon, the above-described methods for determining the formulation orientation of the dosage forms by detecting the color at the narrow and rounded ends corresponding to the dispensing end and push end of the tablet are not satisfactory.

Pharmaceutical manufacturing in general requires high speed, efficiency and accuracy and it is generally desirable to provide as many automated steps as possible. It would be an advance in the art to develop rapid and accurate automated color-detection methods and apparatus for determining the formulation orientation of multi-layer capsule-shaped osmotic dosage forms with respect to different internal formulation layers proximate to the opposite narrow and rounded ends of the tablets.

BRIEF SUMMARY OF THE INVENTION

One aspect of the present invention pertains to providing methods and apparatus for determining the formulation orientation of multi-layer capsule-shaped osmotic tablets. In a more particular aspect, the present invention pertains to rapidly and accurately determining the formulation orientation of such tablets by including a specific color scheme in the design of the tablets that permits color detection at a spot location on the side of the tablet to be used for determining the formulation orientation.

In another aspect, the present invention pertains to methods of making multi-layer capsule-shaped osmotic tablets having an appropriate color scheme to facilitate determination of the tablet formulation orientation by color detection at a spot location on the side of the tablet.

In accord with the above aspects, by including an appropriate color scheme in multi-layer osmotic tablets, detection of the formulation orientation is achieved by detecting the color at a spot location on a side of the tablet corresponding to one or another formulation layer depending on the formulation orientation of the tablet. An appropriate color scheme includes a first colorant in at least one of the formulation layers of the tablet. Preferably, a first colorant is included in at least one dispensable formulation-forming layer and a second colorant, readily distinguishable from the first colorant, is included in at least one push layer of the tablet. To ensure significant contrast between the dispensable formulation-forming layer(s) and the push layer(s), it is preferred that the first colorant be "light," as defined elsewhere herein, so as to complement a non-colored dispensable formulation-forming layer, if present, and the second colorant be "dark," as defined elsewhere herein, so as to be readily distinguished from either the first colorant or no color. The first and second colorants may be the same colors provided that one is light and one is dark such that the colors are readily distinguishable, as defined elsewhere herein.

The above-described features and advantages, as well as others, will become more apparent from the following detailed disclosure of the invention and the accompanying claims.

DETAILED DESCRIPTION OF THE INVENTION

Figure 1:
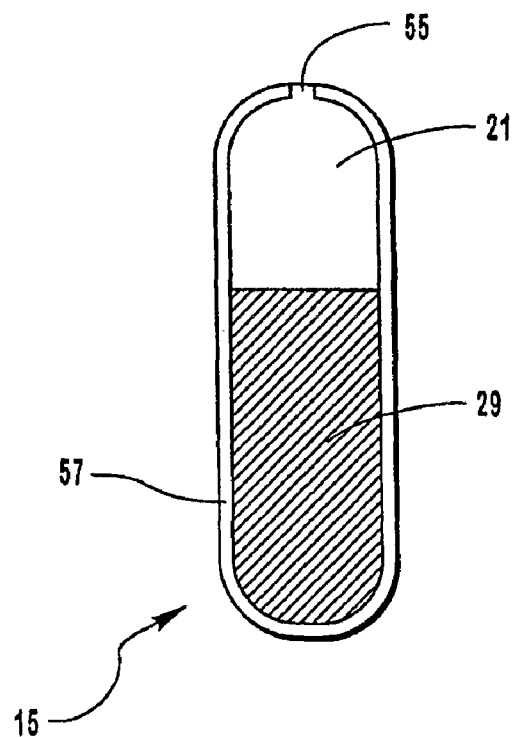
FIG. 1 is a cross-section view of a bi-layer osmotic dosage form requiring determination of the formulation orientation in accord with the present invention.

It has been discovered that capsule-shaped osmotic tablets wherein the formulation layers are oriented such that the dispensing end is at one narrow and rounded end of the capsule-shaped tablet and the push end is at the opposite narrow and rounded end of the capsule-shaped tablet are preferable for certain applications. For purposes of this disclosure, such multi-layer osmotic capsule-shaped tablets shall be referred to as CSTs (capsule-shaped tablets). The advent of CSTs has been found to pose some unique problems for determination of the formulation orientation with a color detector. In the prior art, the differently-colored "ends" i.e., the dispensing end and the push end of the tablet, coincided with the relatively broad and flat front and back surfaces of a conventional tablet-shaped multi-layer osmotic tablet and color detection at one of these surfaces was satisfactory for determining the formulation orientation of the tablet. With CSTs, however, the dispensing end is at one narrow and rounded end of the capsule-shaped tablet and the push end is at the opposite narrow and rounded end. Although differently-colored, the ends are not as readily distinguishable because the ends are narrow and rounded resulting in significant scattering of impinging light from the color detector and reduced accuracy of the color determinations.

As described above, for some processing steps, such as laser drilling of a drug delivery port into the dispensing end of an osmotic tablet, it is necessary to identify the formulation orientation of the CST. By including appropriate colorant(s) in the formulation layers, the different ends are distinguishable by a color detector directed to a spot location on the side of the tablet rather than directed to an end of the tablet. It will be appreciated that a color contrast along the side of a CST can be achieved by adding a colorant to at least one of the formulation layers such that the colorant-containing formulation layer is readily distinguishable from the non-colored (or differently-colored) formulation layer(s).

Typically, a formulation layer that does not have colorant added will be white in color although, depending on the ingredients within the formulation layer, such a formulation layer may have a color other than white. In any case, given the color of a formulation layer with no colorant added, a distinguishable color can be added to the other formulation layer. Alternatively, if desired, a first colorant can be included in one formulation layer and a readily distinguishable second colorant can be included in the other formulation layer.

"Color contrast," as used herein, refers to a difference in colors that is readily and rapidly distinguishable by a suitable color detector. "Readily distinguishable" colors, in general, include colors referred to herein as "light" colors, e.g., colors that complement a white color by having little contrast with a white color, and "dark" colors, e.g., colors that contrast significantly with a white and/or light color, as defined herein.

The phrase "differently-colored," as used herein refers to the readily distinguishable color contrast between either a dark color and no color or a dark color and a light color. For purposes of this disclosure, a formulation layer having "no color" and a formulation layer having a "light color" are not considered to be "differently-colored" whereas either of these layers are "differently-colored" from a dark colored layer.

A wide variety of coloring agents suitable for use in pharmaceutical dosage forms are known and available. The concentration of a suitable colorant that is added to a composition for forming a formulation layer can be widely varied to achieve many shades of color from very dark to very light. Thus, a first and second colorant may be different colors or may be the same color provided that one is used in a manner that effects a light shade and the other a dark shade of the color so that the different "colors" are readily distinguishable as defined herein.

As used herein, the term "colorant" or the phrase "coloring agent" refers to one or more substances, other than excipients, added to a formulation layer composition solely for the purpose of imparting color to that formulation layer within the end product. The term "excipient" refers to pharmaceutically acceptable substances, other than colorants or coloring agents, added to a pharmaceutical dosage form to give suitable consistency or form to the dosage form including diluents, vehicles, carriers, disintegrants, binders, fillers, other processing aids and the like.

It has been discovered that determination of the formulation orientation of multi-layered osmotic capsule-shaped CSTs is accurately and efficiently accomplished by using color indicators for different formulation layers and a color detector directed to a spot location on a side of the tablet rather than at an end of the tablet. By directing the color detector to a spot location on a side of the CST, more accurate color detection is possible because the side does not scatter the impinging light as much as one of the rounded ends does. In addition, tablets of varying lengths and generally similar circumferences can be accommodated with little or no adjustments to the apparatus when the detection is performed at a spot location on the side of the tablet.

Suitable color detectors are known in the art and include various types of incandescent and LED systems. Generally, such detectors include lighting means for generating and directing light to a circumscribed location on a surface and detecting means for recognizing color from the lightwaves that are reflected back to the detector from the spot. Display means for generating a signal, such as an electronic signal, that can be interpreted by a suitable processor are also included. A preferred color detector for use in accord with the present invention is the IDEC SA1J Full Color Recognition Sensor, product of IDEC IZUMI Corporation of Japan. This detector can be set to be responsive to brightness as well as to color differentiation and, thus, can be used to discriminate between many different colors and shades of colors. By directing the sensor to a spot location on a side of the CST, in accord with the present invention, the formulation orientation can be accurately and rapidly determined from the color detected. An appropriate signal is generated and interpreted by a suitable processor for communication to a laser controller to thereby activate the laser as appropriate to drill a delivery port in the dispensing end of the tablet. Tablets that are properly oriented for drilling can be transported to a laser drilling station. Tablets that are improperly oriented can either be removed from the transportation apparatus or can be "passed over" at the laser drilling station and subsequently recycled. Alternatively, as provided in a co-pending patent application, filed May 20, 1999, owned by Alza Corporation and entitled METHODS AND APPARATUS FOR UNIFORMLY ORIEINTING PHARMACEUTICAL DOSAGE FORMS, improperly oriented tablets can have their orientation rectified and then be transported to a laser drilling station in the proper orientation.

An embodiment of a bi-layer oral osmotic dosage form 15 requiring determination of the formulation orientation in accord with the present invention is shown in cross-section in FIG. 1. The components are not drawn to scale. The bi-layer CST core comprises a first component layer 21, containing drug and selected excipients, and a second push layer 29, containing at least one fluid-expandable osmopolymer and optionally containing at least one osmagent along with selected excipients. As indicated by the cross-hatching, the push layer 29 contains a dark colorant such that this layer is readily distinguisbable by color detection on the side of the tablet from the drug-containing layer. The drug-containing layer may be non-colored or may contain a colorant that provides a light color to the layer. A semipermeable membrane 57 surrounds the bi-layer tablet core to form a compartment and a suitably sized orifice 55 is formed through the semipermeable membrane and into the first component layer 21 to permit drug formulation to be released from within the compartment. As described in more detail below, the semipermeable membrane is sufficiently transparent or translucent to permit detection of the underlying differently-colored layers. As illustrated, the orifice 55 is preferably formed in the narrow end of the dosage form comprising the first component layer. In operation, drug is released from the first drug-containing layer at a controlled release rate for an extended time period. Although not shown in FIG. 1, an immediate-release dose of a drug may be provided by applying a drug-containing overcoat to a bi-layer dosage form, if desired, as described elsewhere herein.

Figure 2:
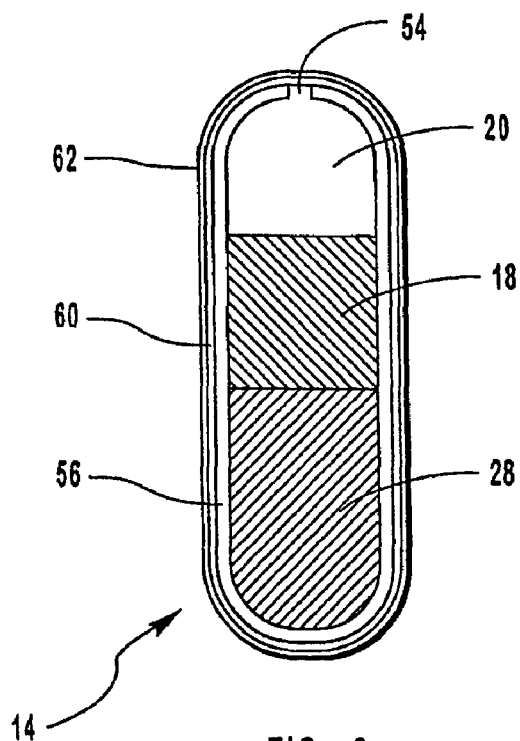
FIG. 2 is a cross-section view of a tri-layer osmotic dosage form requiring determination of the formulation orientation in accord with the present invention.

A preferred embodiment of a tri-layer oral osmotic dosage form 14 requiring determination of the formulation orientation in accord with the present invention is shown in cross-section in FIG. 2. The tri-layer CST core comprises a first dispensable layer 20, containing a selected drug in a pharmaceutically acceptable form along with selected excipients but without any added colorant; a second dispensable layer 18, containing a higher concentration of drug along with selected excipients and a light colorant; and a third push layer 28, containing at least one osmopolymer and optionally containing at least one osmagent along with selected excipients and a colorant that imparts a dark color that is readily distinguishable from the color of the second layer. A semipermeable membrane 56 surrounds the tri-layer tablet core to form a compartment and a suitably sized orifice 54 is formed through the semipermeable membrane and into the first component layer to permit drug formulation to be released from within the compartment. As described in more detail below, the semipermeable membrane is sufficiently transparent or translucent to permit detection of the underlying differently-colored layers. As illustrated, the orifice 54 is preferably formed in the narrow end of the dosage form comprising the first component layer. In operation, through cooperation of the tri-layer osmotic dosage form components, drug is successively released, in a sustained and controlled manner, from the first drug-containing layer and then from the second drug-containing layer at a controlled and, in this example, ascending release rate for an extended time period.

Following drilling of the orifice 54, the preferred embodiment further comprises an immediate-release dose of drug contained within an overcoat 60 applied onto the surface of the tri-layer osmotic dosage form. The drug is mixed with suitable excipients such as, for example, hydroxypropylmethylcellulose, to prepare a solution for coating onto the surface of the semipermeable membrane of the tri-layer osmotic dosage form that will rapidly dissolve and release drug following administration. Also, as shown in FIG. 2, it is also preferred to provide an optional aesthetic overcoat 62 applied onto the surface of the drug-containing overcoat 60. As known in the art, such aesthetic overcoats provide advantages including taste-masking, improved appearance and "glidability" for facilitating swallowing and further processing steps such as printing, packaging, etc. An exemplary embodiment of a tri-layer osmotic dosage form is detailed below in Example 1.

EXAMPLE 1

The first drug-containing layer contained the following (by weight percent): 9.40% methylphenidate hydrochloride, 83.71% polyethylene oxide (Polyox N-80 brand product of Union Carbide, Danbury, Conn.), 5% polyvinylpyrrolidone (Kolidon 29-32 product of BASF Corp., Mt. Olive, N.J.); 1.34% succinic acid; 0.5% stearic acid; and 0.05% butylated hydroxy toluene.

The second drug-containing layer contained the following (by weight percent): 13.65% methylphenidate hydrochloride, 78.80% polyethylene oxide (Polyox N-80 brand product of Union Carbide, Danbury, Conn.), 5% polyvinylpyrrolidone (Kolidon 29-32 product of BASF Corp., Mt. Olive, N.J.); 1.95% succinic acid; 0.5% stearic acid; 0.05% butylated hydroxy toluene; and 0.05% yellow ferric oxide, as coloring agent.

The third layer does not contain drug and is the push layer. The push layer contained the following (by weight percent): 73.7% high molecular weight polyethylene oxide (Polyox 303 brand product of Union Carbide, Danbury, Conn.), 20% sodium chloride; 5% polyvinylpyrrolidone (Kolidon 29-32 brand product of BASF Corp., Mt. Olive, N.J.); 0.25% stearic acid; 0.05% butylated hydroxy toluene; and 1% green ferric oxide, as coloring agent.

Each of the first component layer, second component layer and third push layer were separately prepared into granulated compositions in a fluid bed granulator. The granulated compositions were then compressed sequentially on a rotary tablet press to produce the tri-layer CST cores. For each dosage form, 40 mg of the first component layer granulation and 75 mg of the second component layer granulation were first sequentially filled and tamped at 100 newtons into the die. Then, 90 mg of the third push layer granulation to the die was added to the die and the final compression was performed at 1500 newtons.

The composition of the semipermeable membrane was 83% by weight cellulose acetate (CA 398-10, having an acetyl content of 39.8%, product of Eastman Chemical, Kingsport, Tenn.) and 17% by weight copolymer of ethylene and propylene oxide (Poloxamer 188 brand product of BASF Corp., Mt. Olive, N.J., added as a flux-enhancer. The two ingredients were dissolved in a blend of 99.5% acetone and 0.5% water to form a 5% solids solution. In a pan coater, the solution was then sprayed onto the tri-layer CST cores to a weight of 25.7 mg and a thickness of 4-5 mil.

As noted above, the semipermeable membrane is sufficiently translucent or transparent to permit determination of the formulation orientation by using a color detector directed to a spot location on the side of the CST in accord with the present invention. Accordingly, following determination of the formulation orientation, a 0.76 mm (40 mil) orifice was drilled through the semipermeable membrane at the narrow end of the compartment proximate to the first component layer to thereby form the preferred tri-layer osmotic dosage forms, each containing 14 mg of methylphenidate. Each dosage form was approximately 12 mm long with an approximate diameter of 5.3 mm.

The drug overcoat for providing an immediate-release initial dose of drug contains approximately 30% by weight methylphenidate hydrochloride, approximately 70% by weight hydroxypropylmethylcellulose (Methocel E3 brand name product of Dow Chemical Co., Midland, Mich.), and a trace amount of phosphoric acid (i.e., 20 ml of phosphoric acid added to 87 kg of drug in solution). An aqueous coating solution is prepared by dissolving and mixing the ingredients in water to form a solution with a 10% solids composition. In a pan coater, the solution was then sprayed onto the semipermeable membranes of the tri-layer osmotic dosage forms to a weight of about 14.0 mg comprising an immediate-release dose of methylphenidate of about 4 mg.

The final aesthetic overcoat composition weighed 16.9 mg and contained an underlayer of Opadry II, yellow (brand name product of Colorcon, West Point, Pa. and an overlayer of Opadry, clear, with a trace amount of carnauba wax, a glidant, prepared and applied as follows: first, Opadry II (10%) is suspended in water (90%) and sprayed onto the drug-overcoated dosage forms; next, clear Opadry (5%) is suspended in water (95%) and sprayed onto the drug- and Opadry II-overcoated dosage forms; finally, the dosage forms are tumbled in the coater with the carnauba wax for ten minutes to allow about 100 ppm of wax to be uniformly distributed onto the clear Opadry overcoat.

Figure 3:
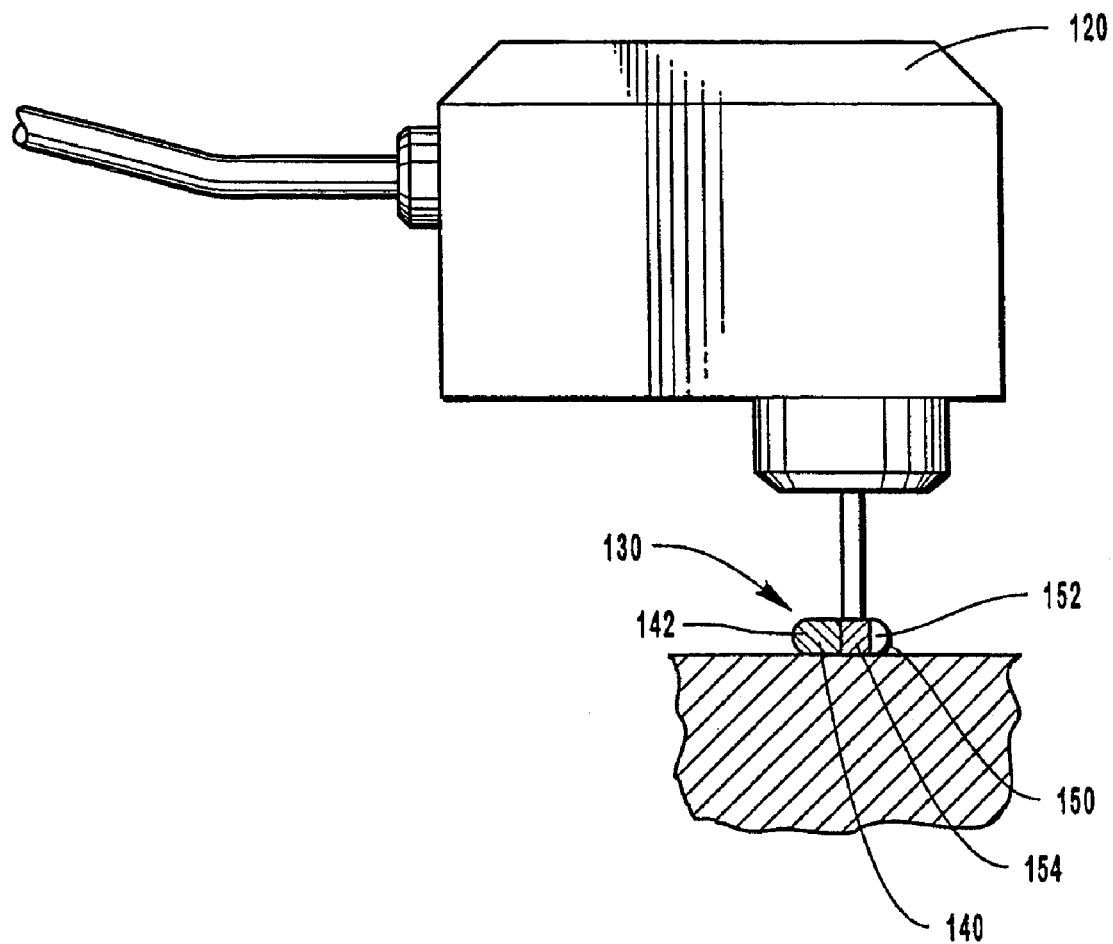
FIG. 3 is a schematic illustration of a method and apparatus in accord with the present invention for determining the formulation orientation of a tri-layered osmotic capsule-shaped tablet.

Turning now to FIG. 3, a color detector 120 is shown in position to detect the color at a spot location on the side of a tri-layered osmotic CST 130 manufactured as described above in Example 1. The tri-layered osmotic CST 130 has the push layer 140, containing 1% green ferric oxide as coloring agent, proximate to the push end 142. The first drug-containing layer 150, containing no colorant and appearing to be white, is proximate to the dispensing end 152. The second drug-containing layer 154, containing 0.05% yellow ferric oxide as coloring agent, is positioned between the other two layers. The color scheme has been adapted to provide a similar light-colored appearance to the two drug-containing layers and a contrasting dark-colored appearance to the push layer. This color scheme is preferred to provide a color contrast between the dispensable formulation-forming layers and the push layers and no color contrast between the dispensable formulation-forming layers.

As shown in FIG. 3, the color detector is directed to a spot location on a side of the CST rather than to a location at either of the narrow and rounded ends. In this manner, an accurate and efficient detection of the color of one or the other layer, or of the color interface between the two layers (depending on the spot location's relationship to the formulation layers), can be achieved. From the color detected, the formulation orientation of the CST can be determined.

It will be appreciated that the spot location can be selected, depending on the size of the CST and the size of each formulation layer, such that the color is determined at a spot location on the tablet that corresponds to one or the other of the dispensable formulation-forming layer(s) (or, possibly, to an interface of these two layers) or to the push layer of the tablet depending on the formulation orientation. Accordingly, the color detector will detect either a light color (including a white color for a layer with no added colorant), corresponding to one or the other of the dispensable formulation-forming layers or to an interface of these layers, or a dark color, corresponding to the push layer. Depending on the color detected, the formulation orientation of the CST can be determined.

It will be appreciated that the spot location is preferably selected, depending on the size of the CST and the size of each formulation layer, such that the color is determined at a location on the tablet that does not encompass an interface of differently-colored layers, i.e., a non-colored or light colored layer with a dark colored layer. For example, if the push layer occupies substantially about half of the internal compartment of the dosage form, a spot location near the center of the tablet should be avoided. Rather, a spot location that is off-center, toward one or the other end of the CST, is preferred such that the color detector sees either the color of the push layer or the readily distinguishable color of one or another dispensable formulation-forming layer, depending on the tablet orientation.

As shown in FIG. 3, a spot location is illustrated that is near the center of the CST but slightly toward the right end. In the exemplary CST 130, the push layer occupies substantially half of the internal compartment of the CST and the second drug-containing layer occupies most of the remaining half of the internal compartment. Accordingly, given the spot location illustrated, the color detector 120 will detect either the dark-colored push layer or the light-colored second layer (as shown). If the spot location were moved to the center of the CST, the color detector would see a dark-light color interface and, the order of the colors would need to be analyzed to determine the formulation orientation of the CST. Since this analysis is more complicated than a simple dark/light color determination, it is preferred to select a spot location that will detect the color of one or another formulation layer as shown in FIG. 3.

While there has been described and pointed out features and advantages of the invention, as applied to present embodiments, those skilled in the art will appreciate that various modifications, changes, additions, and omissions in the descriptions within the specification can be made without departing from the spirit of the invention.

We claim:

1. A method of detecting the formulation orientation of a multi-layer capsule-shaped osmotic tablet comprising
    a first layer containing a drug ingredient and a second layer containing a drug ingredient, wherein at least one of the first and second layers comprises a first colorant;
    a further layer containing a second colorant that is distinguishable from the first colorant or no color, the further layer not containing any drug ingredient;
    wherein the first layer is located at one end of the tablet, the further layer is located at the other end of the tablet, and the second layer is located between the first layer and the further layer, such that the formulation orientation of the tablet can be determined by detecting the color at a spot location on a side of the tablet corresponding to one or another differently colored layer depending on the formulation orientation of the tablet;
    the method comprising the steps of:
    detecting the color at a spot location on a side of the tablet corresponding to one or another layer depending on the formulation orientation of the tablet; and
    determining the formulation orientation of the tablet on the basis of the color detected.

2. The method according to claim 1 wherein at least one of the layers contains a dark colorant.

3. The method according to claim 1 wherein one of the layers contains a dark colorant and, if one of the first and further layers contains the dark colorant, then the other of the first and further layers contains a light color.

4. A method of detecting the formulation orientation of a multi-layer capsule-shaped osmotic tablet having an end portion containing a first formulation layer that contains a drug ingredient, an opposite end portion containing a second formulation layer without a drug ingredient, and at least one intervening formulation layer with a drug ingredient, the method comprising the steps of
    detecting the color at a spot location on a side of the tablet corresponding to the first or second formulation layer depending on the formulation orientation of the tablet, wherein at least one of the formulation layers contains a colorant; and
    determining the formulation orientation of the tablet on the basis of the color detected.

5. The method according to claim 4 wherein one of the formulation layers contains a dark colorant.

6. The method according to claim 4 wherein a formulation layer without a drug ingredient contains a dark colorant and a formulation layer that contains a drug ingredient contains a light colorant.

7. A method of detecting the formulation orientation of a multi-layer capsule-shaped osmotic tablet having an end portion containing a dispensable formulation-forming layer that contains a drug ingredient, an opposite end portion containing an expanding polymer formulation layer, and an intervening layer that contains a drug ingredient, the method comprising the steps of:
    detecting the color at a spot location on a side of the tablet corresponding to one or another formulation layer depending on the formulation orientation of the tablet, wherein at least one of the dispensable formulation-forming layer and the expanding polymer formulation layers contains a colorant; and
    determining the formulation orientation of the tablet on the basis of the color detected.

8. The method according to claim 7 wherein the expanding polymer formulation layer contains a dark colorant.

9. The method according to claim 7 wherein the expanding formulation layer contains a dark colorant and the dispensable formulation-forming layer or the intervening layer contains a light colorant.

10. A method of detecting the formulation orientation of a three-layer capsule-shaped osmotic tablet having an end portion containing a first formulation layer that contains a drug ingredient, a middle portion containing a second formulation layer that contains a drug ingredient, and an opposite end portion containing a third formulation layer without a drug ingredient, the method comprising the steps of
    including a colorant in the first or third formulation layer of the tablet;
    detecting the color at a spot location on a side of the tablet corresponding to one or another differently-colored formulation layer depending on the formulation orientation of the tablet; and
    determining the formulation orientation of the tablet on the basis of the color detected.

11. The method according to claim 10 comprising the steps of:
    including a first colorant in one of the first or second formulation layers of the tablet;
    including a second colorant in the third formulation layer;
    detecting the color at a spot location on a side of the tablet corresponding to one or another differently-colored formulation layer depending on the formulation orientation of the tablet; and
    determining the formulation orientation of the tablet an the basis of the color detected.

12. The method of claim 11 wherein said first colorant is light and said second colorant is dark.

13. A method of detecting the formulation orientation of a three-layer capsule-shaped osmotic tablet having an end portion containing a first dispensable formulation layer, a middle portion containing a second dispensable formulation layer, and an opposite end portion containing an expandable polymer formulation layer, wherein the first and second layers contains a drug ingredient, the method comprising the steps of:
    including a first colorant in one of the first or second dispensable formulation layers of the tablet;
    including a second colorant in the third expandable polymer formulation layer;
    detecting the color at a spot location on a side of the tablet corresponding to one or another differently-colored formulation layer depending on the formulation orientation of the tablet; and
    determining the formulation orientation of the tablet on the basis of the color detected.

14. The method of claim 13 wherein said first colorant is light and said second colorant is dark.

15. A three-layer tablet comprising:
first layer formulation containing a drug ingredient and a second layer containing a drug ingredient, one of the first or second layers also containing a first colorant;
a third layer formulation containing a second colorant that is distinguishable from the first colorant or from no color and not containing any drug ingredient wherein the first, second and third layers are compressed into capsule-shaped osmotic tablet having the first layer formulation located at one end of the capsule-shaped osmotic tablet and the third layer formulation located at the other end of the capsule-shaped osmotic tablet and the second layer located between the first layer formulation and the third layer formulation such that the formulation orientation of the tablet can be determined by detecting the color at a spot location on a side of the tablet corresponding to one or another differently-colored formulation layer depending on the formulation orientation of the tablet and wherein the formulation orientation of the tablet is detected by a color detector directed at the spot location on the side of the tablet.

16. The tablet of claim 15 wherein the first colorant is light and the second colorant is dark.

17. The tablet of claim 16 further comprising a membrane surrounding the compressed layers through which the first and second colorant are detectable.

18. The tablet of claim 17 further comprising a delivery port drilled into the membrane at a location proximate to the first layer.

19. The tablet of claim 18 further comprising a drug overcoat applied onto the surface of the membrane.

20. A three-layer tablet comprising:
a first layer formulation containing a drug ingredient and not containing any colorant;
a second layer formulation containing a drug ingredient and a first colorant, the first colorant being complementary to no color;
a third layer formulation containing a second colorant that is distinguishable from the first colorant or from no color and not containing any drug ingredient wherein the first, second and third layers are compressed into a capsule-shaped osmotic tablet wherein the first layer formulation is located at one end of the capsule-shaped osmotic tablet and the third layer formulation is located at the other end of the capsule-shaped osmotic tablet and the second layer is located between the first layer formulation and the third layer formulation such that the formulation orientation of the tablet can be determined by detecting the color at a spot location on a side of the tablet corresponding to one or another differently-colored formulation layer depending on the formulation orientation of the tablet; and
wherein the formulation orientation of the tablet is detected by a color detector directed at the spot location on the side of the tablet.

21. The tablet of claim 20 wherein the first colorant is light and the second colorant is dark.

22. The tablet of claim 21 further comprising a membrane surrounding the compressed layers through which the first and second colorant are detectable.

23. The tablet of claim 22 further comprising a delivery port drilled into the membrane at a location proximate to the first layer.

24. The tablet of claim 23 further comprising a drug overcoat applied onto the surface of the membrane.

* * * * *

UNITED STATES PATENT AND TRADEMARK OFFICE
CERTIFICATE OF CORRECTION

PATENT NO.           : 8,323,691 B2                                    Page 1 of 1
APPLICATION NO.      : 12/402075
DATED                : December 4, 2012
INVENTOR(S)          : Johan B. Geerke and Steven F. Stone It is certified that error appears in the above-identified patent and that said Letters Patent is hereby corrected as shown below:

<u>Column 9,</u>
Claim 3, line 42, delete "color." and insert -- colorant. --.

<u>Column 10,</u>
Claim 11, line 44, delete "tablet an the" and insert -- tablet on the --.

Signed and Sealed this
Fifth Day of April, 2016

Michelle K. Lee
*Director of the United States Patent and Trademark Office*